United States Patent
Hosoi

(10) Patent No.: US 7,156,517 B2
(45) Date of Patent: Jan. 2, 2007

(54) OPTOMETRIC APPARATUS

(75) Inventor: Yoshinobu Hosoi, Gamagori (JP)

(73) Assignee: Nidek Co., Ltd., Gamagori (JP)

( * ) Notice: Subject to any disclaimer, the term of this patent is extended or adjusted under 35 U.S.C. 154(b) by 0 days.

(21) Appl. No.: 11/284,849

(22) Filed: Nov. 23, 2005

(65) Prior Publication Data
US 2006/0114413 A1 Jun. 1, 2006

(30) Foreign Application Priority Data
Nov. 30, 2004 (JP) ............... 2004-347217

(51) Int. Cl.
*A61B 3/02* (2006.01)
*A61B 3/00* (2006.01)
(52) U.S. Cl. .............. 351/222; 351/200; 351/205
(58) Field of Classification Search ........ 351/201, 351/204, 205, 245, 222, 200
See application file for complete search history.

(56) References Cited

U.S. PATENT DOCUMENTS

| 2,329,907 | A | * | 9/1943 | Jobe et al. ............ 351/217 |
| 5,130,548 | A | * | 7/1992 | Sano et al. ........... 250/461.1 |
| 5,281,984 | A | | 1/1994 | Burton et al. |
| 2003/0090630 | A1 | | 5/2003 | Biggins et al. |

* cited by examiner

Primary Examiner—Charles A Marmor, II
Assistant Examiner—John R Sanders
(74) Attorney, Agent, or Firm—Oliff & Berridge, PLC

(57) ABSTRACT

A subjective optometric apparatus comprises: right-eye and left-eye examination units, each including a test window and optical elements that are manually selectively disposed in the test window; an indicator provided in each examination unit, the indicator being arranged to indicate information on the optical element disposed in the test window and generate fluorescence by ultraviolet light; and an illumination unit which includes a light source and illuminates the indicator with the ultraviolet light.

4 Claims, 3 Drawing Sheets

OPTOMETRIC APPARATUS

BACKGROUND OF THE INVENTION

1. Field of the Invention

The present invention relates to an optometric apparatus for subjectively examining (measuring) refractive power and others of examinee's eyes.

2. Description of Related Art

There are known optometric apparatuses called "refractor" and "phoropter" for subjectively examining (measuring) refractive power and others of eyes of an examinee. These apparatuses are arranged to manually selectively dispose optical elements such as sphere lenses and cylinder lenses in front of the eyes of the examinee, who views optotypes or charts presented forward of his/her eyes through the disposed optical elements, to subjectively examine (measure) the refractive power and others based on for example how the optotypes or charts are visible to the examinee. Such subjective optometric apparatuses are often used in a dark room. Accordingly, an examiner has to illuminate the information such as power of the optical elements and other information indicated on the apparatus with a penlight or the like in order to visually recognize them. To avoid such troublesomeness, there has recently been proposed an apparatus provided with a function for illuminating the indicated optical element information (e.g., U.S. Pat. No. 5,281,984). In this apparatus, the optical element information is illuminated from inside by light from a light source built in the apparatus.

However, illumination by the light source that emits general white light can easily make the indicated optical element information visible, whereas it would cause a problem that the inside of the dark room is lightened.

SUMMARY OF THE INVENTION

The present invention has been made in view of the above circumstances and has an object to provide an optometric apparatus with a simple structure to make information such as power of optical elements indicated on the apparatus visible even in a dark room.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a subjective optometric apparatus comprising: right-eye and left-eye examination units, each including a test window and optical elements that are manually selectively disposed in the test window; an indicator provided in each examination unit, the indicator being arranged to indicate information on the optical element disposed in the test window and generate fluorescence by ultraviolet light; and an illumination unit which includes a light source and illuminates the indicator with the ultraviolet light.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
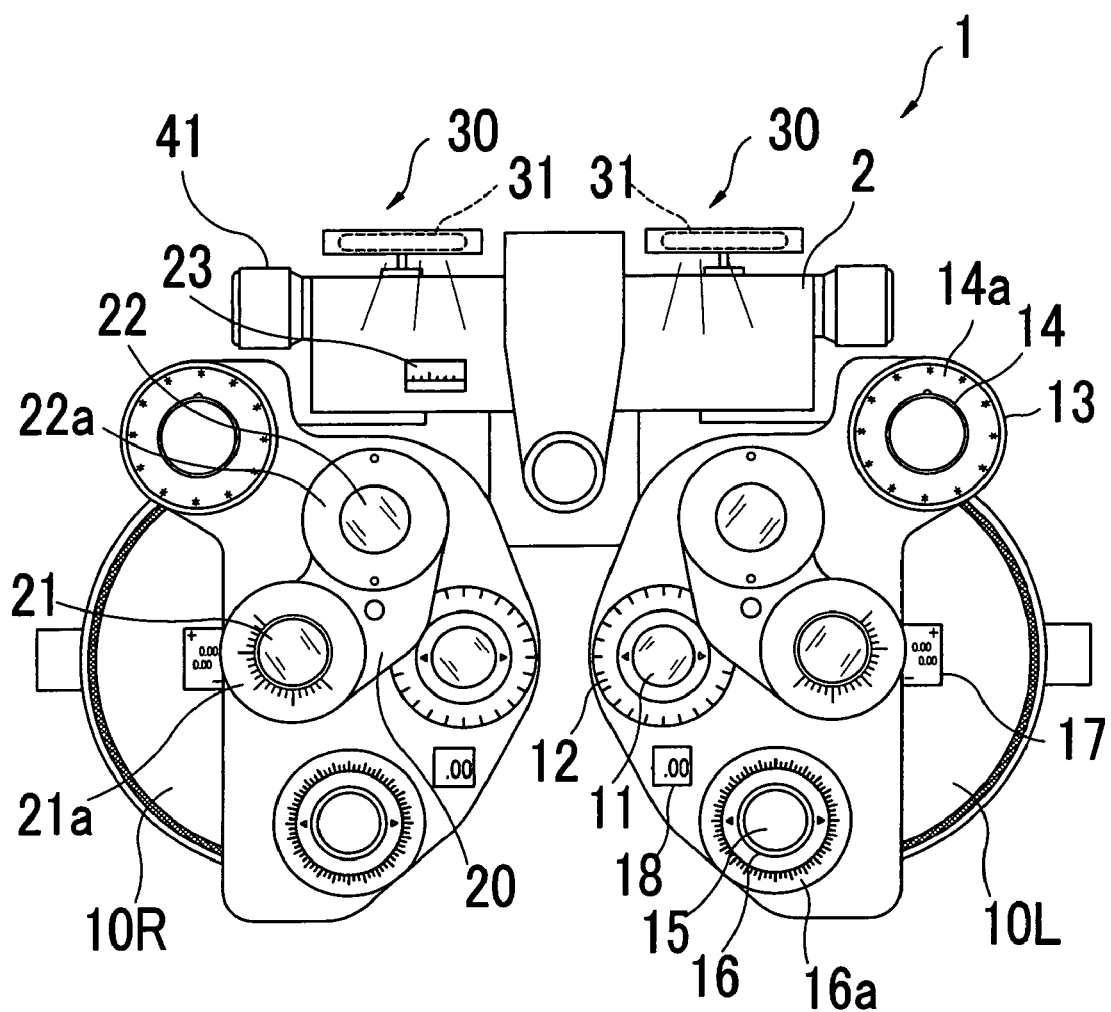
FIG. 1 is a perspective external view of a subjective optometric apparatus in an embodiment, as viewed from an examiner's side.
Figure 2:
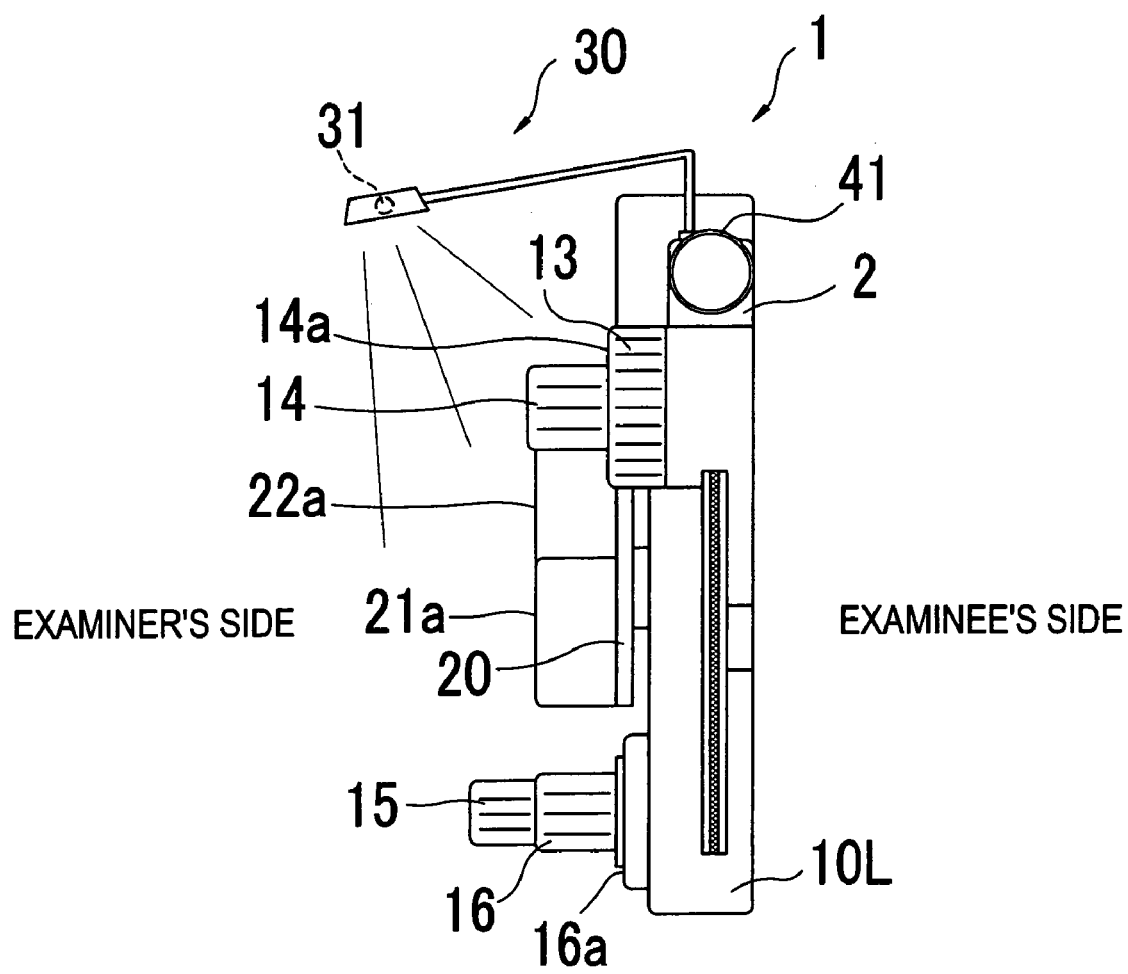
FIG. 2 is a schematic external side view of the optometric apparatus.

A detailed description of a preferred embodiment of the present invention will now be given referring to the accompanying drawings. FIG. 1 is a schematic external view of a subjective optometric apparatus in the present embodiment. FIG. 2 is a schematic external side view of the optometric apparatus of FIG. 1.

An optometric apparatus 1 includes a pair of left-eye examination unit 10L and right-eye examination unit 10R which are symmetrically structured, and a supporting unit 2 which supports the examination units 10L and 10R suspending therefrom. Each of the examination units 10L and 10R is provided with a test window 11, in which various types of optical elements are selectively disposed as mentioned later.

Further, in the test windows 11 on the examiner's side and examinee's side, transparent protecting members such as resin, glass, and the like are set to prevent dust and others from entering the examination units 10L and 10R. At least the protecting member placed on the examinee's side is applied with a coating that blocks ultraviolet light. The protecting member itself may be made of a material that blocks ultraviolet light.

In the examination units 10L and 10R, respectively, there are mounted a plurality of lens disks not shown, in each of which a plurality of various optical elements such as a sphere lens, an auxiliary lens, and a cylinder (astigmatic) lens are arranged. Each lens disk is connected to operating elements (members) through a driving mechanism not shown such as gears. The operating elements include a sphere power change knob (dial) 13, an auxiliary lens change knob 14, a cylinder (astigmatic) power change knob 15, a cylinder (astigmatic) axis angle change knob 16, and others, which are provided on the examiner's-side external surface of each of the examination units 10L and 10R. By operation (rotation) of the knobs 13, 14, 15, and others, the lens disks are rotated to dispose a desired optical element in the test window 11. By operation (rotation) of the knob 16, the cylinder lens is rotated with respect to the lens disk, thereby changing the cylinder axis angle thereof.

Provided around the knob 14 is an indicator 14a for indicating the type of the auxiliary lens disposed in the test window 11. Provided around the knob 16 is an indicator 16a for indicating the cylinder axis angle of the cylinder lens disposed in the test window 11. Further, an indicator 17 for indicating the sphere power of the sphere lens disposed in the test window 11 and an indicator 18 for indicating the cylinder power of the cylinder lens disposed in the test window 11 are provided in the examination units 10L and 10R on respective examiner's-side external surfaces. Around each test window 11, similarly, an indicator 12 is provided to indicate the cylinder axis angle of the cylinder lens disposed in the test window 11.

A turret 20 is mounted on the examiner's-side external surface of each of the examination units 10L and 10R. On the turret 20, a rotary prism 21 and a cross cylinder lens 22 are placed through holding members, which are selectively disposed onto the test window 11 on the examiner's side. The rotary prism 21 and the cross cylinder lens 22 are placed on the turret 20 so that they are rotatable through the holding members. The holding member for the rotary prism 21 is provided with an indicator 21a which indicates a placed (rotated) state of the rotary prism 21. The holding member for the cross cylinder lens 22 is provided with an indicator 22a which indicates a placed (rotated) state of the cross cylinder lens 22.

Furthermore, an indicator 23 for indicating a distance between the test windows 11 of the examination units 10L and 10R (a pupillary distance (PD)) is provided on the examiner's-side external surface of the supporting unit 2. The indicator 23 indicates an interval between the examination units 10L and 10R (that is, a distance between their test windows 11), which is changed by operation of a PD adjustment knob 41.

The indicators 12, 14a, 16a, 17, 18, 21a, 22a, and others, which indicate information on the optical elements, and other indicators such the indicator 23 are applied with coating or paint which will generate fluorescence by ultraviolet light, which will be mentioned in detail.

Each of illumination units 30 provided on the supporting unit 2 includes a light source 31 which emits ultraviolet light such as black light and a switch not shown for turning on/off the light source 31. The light source 31 is located in a position to illuminate each indicator as shown in FIGS. 1 and 2. In the present embodiment, two illumination units 30 are arranged on the supporting unit 2 to illuminate the examiner's-side external surfaces of the examination units 10L and 10R from above. However, the number and position of illumination units 30 (light sources 31) are not limited to those shown in FIG. 1 as long as the indicators provided on the examiner's-side external surfaces of the examination units 10L and 10R and the supporting unit 2 respectively can be illuminated. For instance, the illumination unit 30 may be provided on the side of the examination units 10L and 10R to illuminate the examiner's-side external surface of the examination units 10L and 10R from obliquely front. Further, the illumination unit 30 may be provided in an arm, a table, or the like supporting the apparatus 1. It is to be noted that the light source 31 may be of any type, e.g., a lamp type, an LED type.

Figure 3:
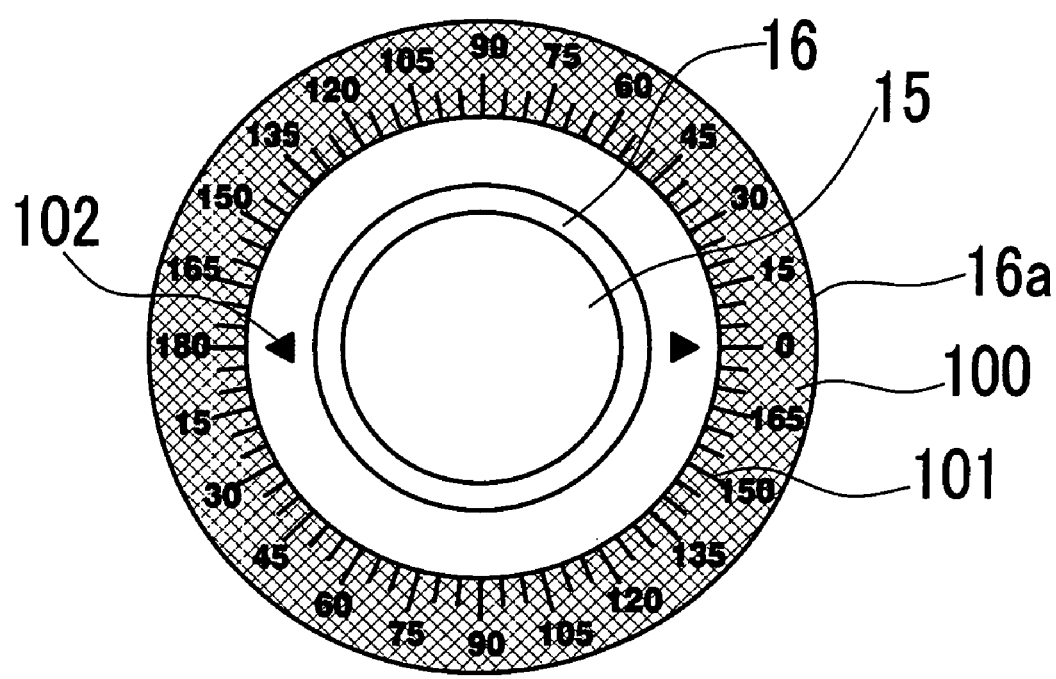
FIG. 3 shows an example that an indicator of a knob is applied with fluorescent coating.

FIG. 3 shows an example that the indicator 16a surrounding the knob 16 is applied with a fluorescent coating. A base 100 of the indicator 16a is applied with a fluorescent coating (designated by cross hatching in FIG. 3) that has a whitish color under visible light and generates a bluish fluorescence when subjected to irradiation of ultraviolet light, and a scale 101 for cylinder axis angles is printed in black, red, or other color different from the fluorescent coating or engraved. A flange of the knob 16 is provided with arrows 102 printed with a fluorescent coating. Based on the position of the arrow 102 with respect to the scale 101, the cylinder axis angle of the cylinder lens selectively disposed in the test window 11 by rotation of the knob 16 becomes visible. Other indicators are structured as with the indicator 16a.

By use of the fluorescent coating that has a whitish color under visible light whereas it generates a bluish fluorescence when subjected to irradiation of ultraviolet light, the indicators (information on the optical elements) easily becomes visible even in either of a normal bright room and a dark room.

In the present embodiment, the fluorescent coating is applied on the base of the indicator and the information on the optical element is printed or engraved thereon. Alternatively, the information on the optical element may be printed with a fluorescent coating directly on the base of the indicator. In this case, the color of the fluorescent coating under visible light has to be appropriately selected so that the information on the optical element is easily visible even outside the dark room. In case the information on "plus power" and "minus power" is indicated as in the indicator 17, further, fluorescent coatings that generate fluorescence in different colors may be used.

The operation of the optometric apparatus constructed as above will be briefly explained as blow.

In case the examination using the optometric apparatus 1 is to be performed in the dark room, the switch not shown of the illumination unit 30 is operated to turn on the light source 31. When the light source 31 is turned on, thus irradiating ultraviolet light to the examiner's side external surfaces of the examination units 10L and 10R, the fluorescent coatings applied or printed on the indicators 12, 14a, 16a, 17, 18, 21a, 22a, 23, and others generate fluorescence. These fluorescent coatings produce soft light, which will not light up the dark room more than necessary. Thus, such fluorescence is unlikely to cause trouble in the examination. The protecting member provided in each test window 11 blocks ultraviolet light, so that the ultraviolet light from each light source 31 can be prevented from entering the examinee's eye.

In case a test optotype is presented forward of the examinee's eye by operation of an optotype presenting device not shown, the optical elements of various types are selectively disposed in the test window 11 by operation of the knobs 13, 14, 15, 16, and others. Thus, the examination on the examinee's eye is performed.

As mentioned above, the light source 31 used in the present embodiment is a light source such as a black light or the like which emits ultraviolet light including no visible light. Alternatively, there may be used a light source such as a black light which emits ultraviolet light including visible light having a wavelength of about 400 nm so that an ON/OFF state of the light source is visible.

In the present embodiment, each illumination unit 30 includes the switch for turning on/off the light source 31. In an alternative, a sensor may be provided for detecting motions of the hands of the examiner in the vicinity of the apparatus 1. Based on a detection result by the sensor, the light source 31 may automatically be turned on during examination and turned off other than during the examination.

In the present embodiment, furthermore, a structure of reflection-type fluorescence is adopted; in which ultraviolet light is irradiated from outside to cause the indicator to generate fluorescence. Alternatively, a structure of transmission-type fluorescence may be adopted; in which ultraviolet light is irradiated from inside to make the indicator generate fluorescence. In this case, the indicator has to be made of a material that allows ultraviolet light to pass therethrough, and a transmission-type fluorescent coating has to be used.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. A subjective optometric apparatus comprising:
right-eye and left-eye examination units, each including a test window provided with a transparent protecting member which is applied with a coating that blocks ultraviolet light or which is made of a material that blocks ultraviolet light and optical elements that are manually selectively disposed in the test window;

an indicator provided in each examination unit, the indicator being arranged to indicate information on the optical element disposed in the test window and generate fluorescence by ultraviolet light; and an illumination unit which includes a light source and illuminates the indicator from outside of the examination unit with ultraviolet light.

2. The optometric apparatus according to claim 1, wherein a fluorescent coating is applied or printed on the indicator.

3. The optometric apparatus according to claim 2, wherein the indicator includes a base applied with the fluorescent coating, and the information on the optical element is printed or engraved on the base.

4. A subjective optometric apparatus comprising:

right-eye and left-eye examination units, each including a test window provided with a transparent protecting member which is applied with a coating that blocks ultraviolet light or which is made of a material that blocks ultraviolet light and optical elements that are manually selectively disposed in the test window;

an indicator provided in each examination unit, the indicator being arranged to indicate information on the optical element disposed in the test window and generate fluorescence by ultraviolet light;

an illumination unit which includes a light source and illuminates the indicator unit with ultraviolet light; and a sensor which detects motions of an examiner in the vicinity of the apparatus, wherein the light source of the illumination unit is turned on/off based on a detection result of the sensor.

* * * * *